United States Patent
Schmidt et al.

(10) Patent No.: US 10,030,105 B2
(45) Date of Patent: Jul. 24, 2018

(54) LOW MOLECULAR WEIGHT PRODUCTS AND USE THEREOF AS REVERSIBLE OR PERMANENT LOW-TEMPERATURE CROSSLINKING AGENT IN DIELS-ALDER REACTIONS

(75) Inventors: Friedrich Georg Schmidt, Haltern am See (DE); Stefan Hilf, Rodenbach (DE); Emmanouil Spyrou, Schermbeck (DE); Jiawen Zhou, Moers (DE); Nathalie Guimard, Saarbruecken (DE); Christopher Barner-Kowollik, Stutensee (DE); Kim Klaus Oehlenschlaeger, Hockenheim (DE); Andre Hennig, Ingelheim (DE)

(73) Assignee: Evonik Degussa GmbH, Essen (DE)

( * ) Notice: Subject to any disclaimer, the term of this patent is extended or adjusted under 35 U.S.C. 154(b) by 349 days.

(21) Appl. No.: 14/234,936

(22) PCT Filed: Jun. 29, 2012

(86) PCT No.: PCT/EP2012/062683
§ 371 (c)(1),
(2), (4) Date: Jan. 24, 2014

(87) PCT Pub. No.: WO2013/017349
PCT Pub. Date: Feb. 7, 2013

(65) Prior Publication Data
US 2014/0163165 A1     Jun. 12, 2014

(30) Foreign Application Priority Data
Jul. 29, 2011 (DE) .......................... 10 2011 080 131

(51) Int. Cl.
*C08L 77/00* (2006.01)
*C08G 79/04* (2006.01)
(Continued)

(52) U.S. Cl.
CPC ............ *C08G 79/04* (2013.01); *C07C 271/24* (2013.01); *C07D 251/30* (2013.01); *C09D 4/00* (2013.01); *C09J 4/00* (2013.01)

(58) Field of Classification Search
CPC ... C07C 271/24; C07C 251/00; C07C 235/00; C07C 233/00
(Continued)

(56) References Cited

U.S. PATENT DOCUMENTS 3,275,679 A * 9/1966 Brotherton ............ C07C 263/16
526/280
3,283,032 A  11/1966 Martin et al.
(Continued)

FOREIGN PATENT DOCUMENTS

DE   40 32 187 A1   4/1992
JP   51-127002 A    11/1976
(Continued)

OTHER PUBLICATIONS

U.S. Appl. No. 14/234,936, filed Jan. 24, 2014, US2014/0163165 A1, Schmidt, et al.
(Continued)

*Primary Examiner* — Jane L Stanley
(74) *Attorney, Agent, or Firm* — Oblon, McCelland, Maier & Neustadt, L.L.P.

(57) ABSTRACT

The invention relates to low molecular mass products and to the use thereof as reversible or permanent low-temperature crosslinkers in Diels-Alder reactions.

18 Claims, 1 Drawing Sheet a)

Decrease of $M_n$ with increasing reaction time (a) of the rDA reaction of 3 in acetonitrile ($c_7^0$ = 20 mg mL$^{-1}$) at 120, 140 and 160°C.

(51) Int. Cl.
*C09D 4/00* (2006.01)
*C09J 4/00* (2006.01)
*C07C 271/24* (2006.01)
*C07D 251/30* (2006.01)

(58) Field of Classification Search
USPC .......................................................... 524/606
See application file for complete search history.

(56) References Cited

U.S. PATENT DOCUMENTS

| | | | |
|---|---|---|---|
| 3,637,557 A * | 1/1972 | Little | C08G 65/263 |
| | | | 252/77 |
| 5,059,655 A * | 10/1991 | Martz | C08G 18/831 |
| | | | 525/131 |
| 2010/0099798 A1 | 4/2010 | Costanzo et al. | |
| 2011/0028712 A1 * | 2/2011 | De Pater | C07C 67/52 |
| | | | 540/349 |
| 2012/0082840 A1 | 4/2012 | Herr et al. | |
| 2012/0289657 A1 | 11/2012 | Hilf et al. | |
| 2012/0309895 A1 | 12/2012 | Schmidt et al. | |
| 2013/0172480 A1 | 7/2013 | Schmidt et al. | |
| 2013/0303678 A1 | 11/2013 | Hilf et al. | |
| 2013/0323993 A1 | 12/2013 | Schmitt et al. | |
| 2014/0121327 A1 | 5/2014 | Schmidt et al. | |

FOREIGN PATENT DOCUMENTS

| | | |
|---|---|---|
| JP | 60-214766 A | 10/1985 |
| JP | 6-263704 A | 9/1994 |
| JP | 2002-294095 A | 10/2002 |
| JP | 2005-529959 A | 10/2005 |
| WO | WO 98/16497 A1 | 4/1998 |
| WO | WO 2004/018001 A1 | 3/2004 |
| WO | 2010 144774 A2 | 12/2010 |
| WO | 2012 065786 A1 | 5/2012 |

OTHER PUBLICATIONS

U.S. Appl. No. 14/651,317, filed Jun. 11, 2015, Barner-Kowollik, et al.

International Search Report dated Oct. 5, 2012 in PCT/EP2012/062683 filed Jun. 29, 2012.

Office Action dated Mar. 22, 2016 in Japanese Patent Application No. 2014-523251 (submitting English translation only).

Yutaka Mori, et al., "Molecular Arrangement and Photoreaction of Sorbamides and Hexadienyl Carbamates with Various N-Substituents in the Solid State" Crystal Growth & Design, vol. 7, No. 7, 2007, pp. 1356-1364 and Cover Page.

Martin Reinecke, et al., "Renewable resources, 1 Branching and crosslinking of an unsaturated oligoester with furfurylamides and sorbic acid amides via Diels-Alder additions" Makromolekulare Chemie, vol. 194, No. 8, 1993, pp. 2385-2393 and Cover Page.

Martin Reinecke, et al., "Renewable resources, 2 Poly-Diels-Alder additions with disorboylamides as bisdienes and a dimaleoylamide as bisdienophile" Macromolecular Chemistry and Physics; vol. 195, No. 7, 1994, pp. 2445-2455 and Cover Page.

Klaus Banert, et al., "Diastereoselective Tandem Diels-Alder Macrocyclizations Starting from Sorbyl or Sorboyl Derivatives" Synlett, No. 4, 2008; pp. 535-538 and Cover Pages.

Guillaume Le Baut, et al., "Polyenic acids: I. Antifungal and bacteriostatic activities of 2,4-hexadienoic acid derivatives" European Journal of Medicinal Chemistry, vol. 18, No. 5, 1983, pp. 441-445 and Cover Pages (with English Abstract).

Ilyas Washington, et al., "Superoxidation of Bisretinoids" Angewandte Chemie International Edition, vol. 44, No. 43, 2005, pp. 7097-7100 and Cover Page.

Stefano Manfredini, et al., "Retinoic Acid Conjugates as Potential Antitumor Agents: Synthesis and Biological Activity of Conjugates with Ara-A, Ara-C, 3(2H)-Furanone, and Aniline Mustard Moieties" Journal of Medicinal Chemistry, vol. 40, No. 23, 1997, pp. 3851-3857 and Cover Page.

Dimitra Hadjipavlou-Litina, et al., "Does conjugation of antioxidants improve their antioxidative/anti-inflammatory potential?" Bioorganic & Medicinal Chemistry, vol. 18, No. 23, 2010, pp. 8204-8217 and Cover Page.

Renata Vasques da Silva, et al., "Antifungal amides from *Piper arboreum* and *Piper tuberculatum*" Phytochemistry, vol. 59, No. 5, 2002, pp. 521-527 and Cover Page.

Leslie M. Werbel, et al., "Derivatives of 5-Phenyl-2,4-pentadienoic Acid as Potential Antimalarial Agents" Journal of Medicinal Chemistry, vol. 11, No. 5, 1968, pp. 1073-1074 and Cover Page.

U.S. Appl. No. 14/360,442, filed May 23, 2014, Schmidt, et al.
U.S. Appl. No. 14/363,055, filed Jun. 5, 2014, Schmidt, et al.

* cited by examiner

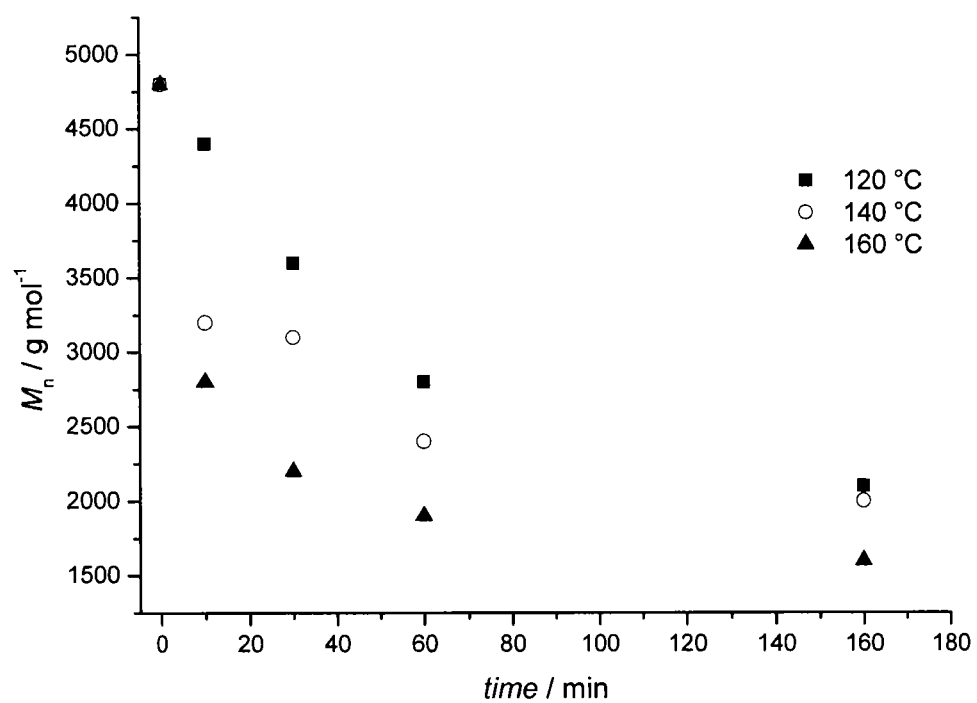
Decrease of $M_n$ with increasing reaction time (a) of the rDA reaction of 3 in acetonitrile ($c_7^0$ = 20 mg mL$^{-1}$) at 120, 140 and 160°C.

LOW MOLECULAR WEIGHT PRODUCTS AND USE THEREOF AS REVERSIBLE OR PERMANENT LOW-TEMPERATURE CROSSLINKING AGENT IN DIELS-ALDER REACTIONS

CROSS REFERENCE TO RELATED APPLICATION

This application is a 371 of PCT/EP2012/062683, filed on Jun. 29, 2012, and claims priority to German Patent Application 10 2011 080 131.6, filed on Jul. 29, 2011.

The invention relates to low molecular mass products and to their preparation and use as reversible or permanent crosslinkers in polymers or polymer networks where the linking or crosslinking of the resultant polymers is brought about via Diels-Alder reactions.

Methods for the reversible crosslinking of polymers are of great interest for a broad field of applications. In adhesive applications, for example, diverse possibilities for the automotive industry or the semiconductor industry have been described. In the context of the construction of machines, precision mechanical devices, or in the building industry as well, however, such adhesives are of interest.

Besides adhesive applications, reversibly crosslinkable polymers may also be of interest in sealants, coating materials such as varnishes or paints, or in the production of mouldings for example via rapid prototyping methods.

The best-known crosslinker molecules for Diels-Alder crosslinking reactions are the bismaleimide units (COMPIMIDE® from Evonik AG) that have already been available commercially for a considerable time.

For a number of years, primarily within academia, methods for constructing block copolymers have been researched under the generic heading of "click chemistry". In this chemistry, two different homopolymers with linkable end groups are combined with one another and are joined to one another by means, for example, of a Diels-Alder reaction, Diels-Alder-analogous reaction or another cycloaddition. The objective of this reaction is to construct thermally stable, linear and possibly high molecular mass polymer chains. Inglis et al. (Macromolecules 2010, 43, pp. 33-36), for example, describe, for this purpose, polymers with cyclopentadienyl end groups which are obtainable from polymers prepared by means of ATRP. These cyclopentadiene groups are able to react very rapidly in hetero-Diels-Alder reactions with polymers which carry electron-deficient dithioesters as end groups (Inglis et al. Angew. Chem. Int. Ed. 2009, 48, pp. 2411-2414).

The use of monofunctional RAFT polymers for linking with monofunctional polymers which a dihydrothiopyran group by way of a hetero-Diels-Alder reaction is found in Sinnwell et al. (Chem. Comm. 2008, 2052-2054). This method can be used to realise AB diblock copolymers.

Rapid variants of this hetero-Diels-Alder linkage for the synthesis of AB block copolymers with a dithioester group which is present after a RAFT polymerization, and with a dienyl end group, are described in Inglis et al. (Angew. Chem. Int. Ed. 2009, 48, pp. 2411-14) and in Inglis et al. (Macromol. Rapd Commun. 2009, 30, pp. 1792-98). The analogous preparation of multiarm star polymers is found in Sinnwell et al. (J. Pol. Sci.: Part A: Pol. Chem. 2009, 47, pp. 2207-13).

U.S. Pat. No. 6,933,361 describes a system for producing transparent mouldings that are easy to repair. The system consists of two polyfunctional monomers which polymerize by a Diels-Alder reaction to form a highly dense network. One functionality in this system is a maleimide, and the other functionality is a furan. The thermal switching of a highly dense network of this kind is used for its repair. Crosslinking takes place at temperatures above 100° C. The partial reverse reaction at even higher temperatures.

In Syrett et al. (Polym. Chem. 2010, DOI: 10.1039/b9py00316a), star polymers are described for use as flow improvers in oils. These polymers have self-healing properties that can be controlled by means of a reversible Diels-Alder reaction. For that purpose, monofunctional polymethacrylate arms are combined with polymethacrylates which in the middle of the chain, as a fragment of the initiator employed, possess a group which can be used in a reversible Diels-Alder reaction.

Patent application DE102010001987.9 discloses crosslinkable systems which feature a thermoreversible crosslinking mechanism based on a Diels-Alder or hetero-Diels-Alder reaction. DE102010001992.5 discloses analogous systems which have a controllable viscosity by means of the same thermoreversible mechanism.

U.S. Pat. No. 4,513,125 A discloses a composition for special cathodic electrodeposition coatings, where a polydiene-functionalized epoxy-amine reacts with a polydienophile-functionalized polyisocyanate oligomer at elevated temperatures. The polydienophile-functionalized polyisocyanate oligomers have a functionality of at least 3. Cited specifically are furfuryl alcohol and/or furfurylamine, 2-hydroxymethyl-1,3-butadienes, 2-aminomethyl-1,3-butadiene or mixtures thereof. Sorbic alcohol derivatives, however, are not cited.

Object

It was an object of the present invention to find low molecular mass crosslinker molecules, easy to synthesize and with diverse possible uses, for Diels-Alder reactions at preferably low temperatures, and with the possibility of a retro-Diels-Alder reaction for reversible crosslinkings, these molecules additionally being particularly ecological.

The object has been achieved by the new reaction products of the present invention.

The invention provides a reaction product of

A) at least one isocyanate and/or amine having at least two functional groups per molecule of the general formula 1

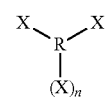

1 with the following definitions:

n=0 or 1,

X=NCO, $NH_2$ or NHA,

A=H, simultaneously or independently of one another alkyl radical having 1 to 16 carbon atoms, cyclic hydrocarbon radical or aromatic hydrocarbon radical, it also being possible for this radical to contain heteroatoms and/or functional groups and/or double bonds, R=aliphatic or cycloaliphatic hydrocarbon radical, which may also contain heteroatoms and/or functional groups and/or double bonds, and B) at least one diene having a functional group of the general formula 2

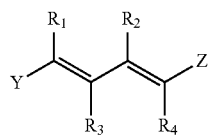

with the following definitions:
Y=$CH_2OH$, COOH, COOA, $CH_2NH_2$ or $CH_2NHA$, and
A, Z and $R^1$-$R^4$=simultaneously or independently of one another alkyl radical having 1 to 16 carbon atoms, cyclic hydrocarbon radical or aromatic hydrocarbon radical, it also being possible for these radicals to contain heteroatoms and/or functional groups and/or double bonds,
where all of the functional groups X of A) have undergone reaction with the equivalent amount of B).

Surprisingly it has been found that the compounds according to the invention can be crosslinked with dienophiles even at room temperature or at only slightly elevated temperatures and that the crosslinking can be made at least 50% reversible at a higher temperature.

It has been found that these systems crosslink very rapidly even at room temperature, optionally with addition of a crosslinking catalyst. It has also been found that these networks can be returned to a thermoplastic state again, simply and almost completely, even at very low temperatures of, for example, somewhat above 80° C. It has additionally been found, very surprisingly, that subsequently a further crosslinking can take place, without further addition of crosslinker and/or catalyst, by means, for example, of pure cooling. A particular effect, furthermore, is that these cycles of crosslinking and conversion back into a thermoplastic can be carried out at least three times, preferably at least five times, without any substantial loss in properties of the network.

Suitable component A) isocyanates are aliphatic, cycloaliphatic and araliphatic, i.e. aryl-substituted aliphatic, diisocyanates, of the kind described, for example, in Houben-Weyl, Methoden der organischen Chemie, Volume 14/2, pages 61-70 and in the article by W. Siefken, Justus Liebigs Annalen der Chemie 562, 75-136, such as 1,2-ethylene diisocyanate, 1,4-tetramethylene diisocyanate, 1,6-hexamethylene diisocyanate (HDI), 2,2,4-trimethyl-1,6-hexamethylene diisocyanate (TMDI), 2,4,4-trimethyl-1,6-hexamethylene diisocyanate (TMDI) and also mixtures thereof, 1,9-diisocyanato-5-methylnonane, 1,8-diisocyanato-2,4-dimethyloctane, 1,12-dodecane diisocyanate, ω,ω'-diisocyanatodipropyl ether, cyclobutene 1,3-diisocyanate, cyclohexane 1,3-diisocyanate, cyclohexane 1,4-diisocyanate, 3-isocyanatomethyl-3,5,5-trimethylcyclohexyl isocyanate (isophorone diisocyanate, IPDI), 1,4-diisocyanatomethyl-2,3,5,6-tetramethylcyclohexane, decahydro-8-methyl-1,4-methanol-naphthalen-2,5-ylenedimethylene diisocyanate, decahydro-8-methyl-1,4-methanol-naphthalen-3,5-ylenedimethylene diisocyanate, hexahydro-4,7-methanoindan-1,5-ylenedimethylene diisocyanate, hexahydro-4,7-methanoindan-2,5-ylenedimethylene diisocyanate, hexahydro-4,7-methanoindan-1,6-ylenedimethylene diisocyanate, hexahydro-4,7-methanoindan-2,5-ylenedimethylene diisocyanate, hexahydro-4,7-methanoindan-1,5-ylene diisocyanate, hexahydro-4,7-methanoindan-2,5-ylene diisocyanate, hexahydro-4,7-methanoindan-1,6-ylene diisocyanate, hexahydro-4,7-methanoindan-2,6-ylene diisocyanate, 2,4-hexahydrotolylene diisocyanate, 2,6-hexahydrotolylene diisocyanate, 4,4'-methylenedicyclohexyl diisocyanate (4,4'-$H_{12}$MDI), 2,2'-methylenedicyclohexyl diisocyanate (2,2'-$H_{12}$MDI), 2,4-methylenedicyclohexyl diisocyanate (2,4-$H_{12}$MDI) or any desired mixtures of these isomers, 4,4'-diisocyanato-3,3',5,5'-tetramethyldicyclohexylmethane, 4,4'-diisocyanato-2,2',3,3',5,5',6,6'-octamethyldicyclohexylmethane, ω,ω'-diisocyanato-1,4-diethyl-benzene, 1,4-diisocyanatomethyl-2,3,5,6-tetramethylbenzene, 2-methyl-1,5-diisocyanato-pentane (MPDI), 2-ethyl-1,4-diisocyanatobutane, 1,10-diisocyanatodecane, 1,5-diisocyanato-hexane, 1,3-diisocyanatomethylcyclohexane, 1,4-diisocyanatomethylcyclohexane and also any desired mixtures of these compounds. Further suitable isocyanates are described in the stated article in the Annalen on page 122 f. Also suitable is 2,5-bis(isocyanatomethyl)bicyclo-[2.2.1] heptane (NBDI) and/or (2,6)-bis(isocyanatomethyl)bicyclo [2.2.1]heptane (NBDI), as the pure substance or as a mix component. These diisocyanates are nowadays generally prepared either by the phosgene route or by the urea method. The products of both methods are equally suitable for use in the process of the invention.

Particular preference is given to using aliphatic and cycloaliphatic diisocyanates. Very particular preference is given to using IPDI, TMDI, HDI and/or $H_{12}$MDI, alone or in mixtures.

Another preferred class of polyisocyanates as component A) are the compounds having more than two isocyanate groups per molecule that are prepared by dimerizing, trimerizing, allophanatizing, biuretizing and/or urethanizing the simple diisocyanates, examples being the reaction products of these simple diisocyanates, such as IPDI, TMDI, HDI and/or $H_{12}$MDI, for example, with polyhydric alcohols (e.g. glycerol, trimethylolpropane, pentaerythritol) and/or polyfunctional polyamines.

Particular preference is also given to using the isocyanurates which are obtainable by trimerizing the simple diisocyanates. Very particular preference is given to using the trimers of IPDI, HDI and/or $H_{12}$MDI, alone or in mixtures.

Also suitable as component A) are aliphatic, cycloaliphatic and araliphatic, i.e. aryl-substituted aliphatic, amines having at least two amino groups in the molecule.

Particularly preferred are diamines selected from 1,3- and 1,4-diaminomethylcyclohexane, hexane-1,6-diamine (HDA), 2,2,4- and/or 2,4,4-trimethylhexane-1,6-diamine and also mixtures thereof, 3-aminomethyl-3,5,5-trimethylcyclohexylamine (isophoronediamine, IPDA), 4,4'-methylenedicyclohexyldiamine, 2,4-methylenedicyclohexyldiamine, 2,2'-methylenedicyclohexyldiamine and also any desired mixtures of these isomers ($H_{12}$MDA), and polyetherdiamines are used. It is also possible to use mixtures of the amines.

Particularly preferred are IPDA, HDA and/or $H_{12}$MDA.

As dienes B), dienes having only one functional group are used, of the general formula 2

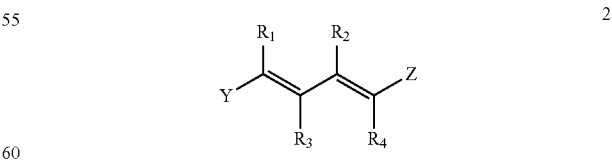

with the following definitions
Y=$CH_2OH$, COOH, COOA, $CH_2NH_2$ or $CH_2NHA$,
where
A, Z and $R^1$-$R^4$=simultaneously or independently of one another alkyl radical having 1 to 16 carbon atoms, cyclic hydrocarbon radical or aromatic hydrocarbon radical, it also being possible for these radicals to contain heteroatoms and/or functional groups and/or double bonds.

The radical Z here is an inert radical, which does not react with component A).

The radical Y reacts with functional groups X of the component A) to give the reaction product.

Particular preference is given to using sorbic alcohol 3 and/or sorbic acid 4.

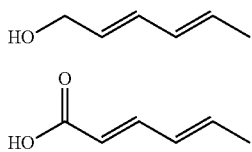

Another preferred class of dienes B) are the so-called retinoids of the following formula 5:

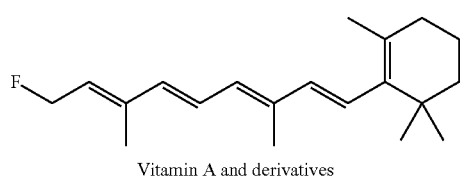

Vitamin A and derivatives

F=OH, COOH, COOK or CHO, where K is alkyl radical having 1 to 6 carbon atoms, cyclic hydrocarbon radical or aromatic hydrocarbon radical, it also being possible for this radical to contain heteroatoms and/or functional groups and/or double bonds, preferably of the formula 6:

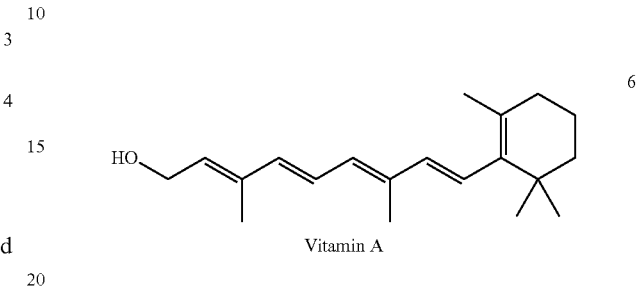

Vitamin A

For the skilled person it is understandable that the functional groups of components A) and B) must be selected such that they react with one another.

As an example of a reaction product according to the invention, it is possible here to recite the reaction of sorbic alcohol with isophorone diisocyanate to give a difunctional diene unit amenable to the Diels-Alder reaction:

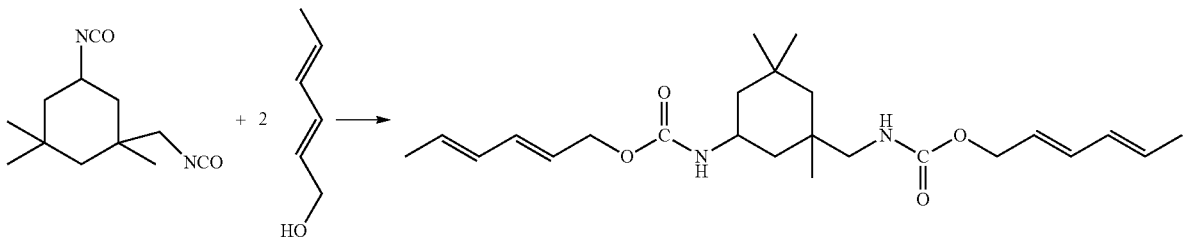

As an example of a reaction product according to the invention with trimers—isocyanurates—it is possible here to recite the reaction of sorbic alcohol with isophorone isocyanurate to give a trifunctional diene unit amenable to the Diels-Alder reaction:

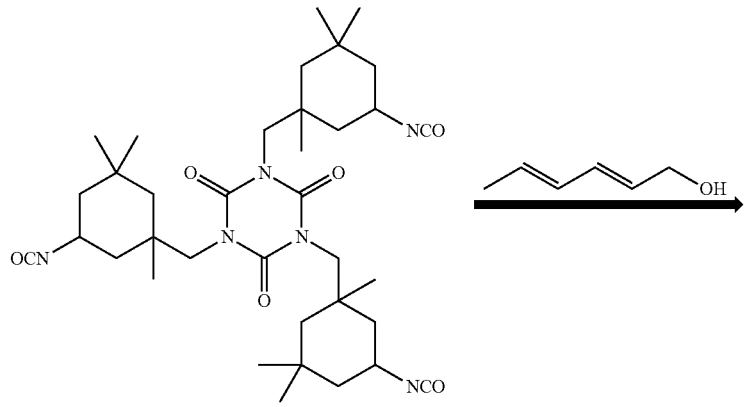

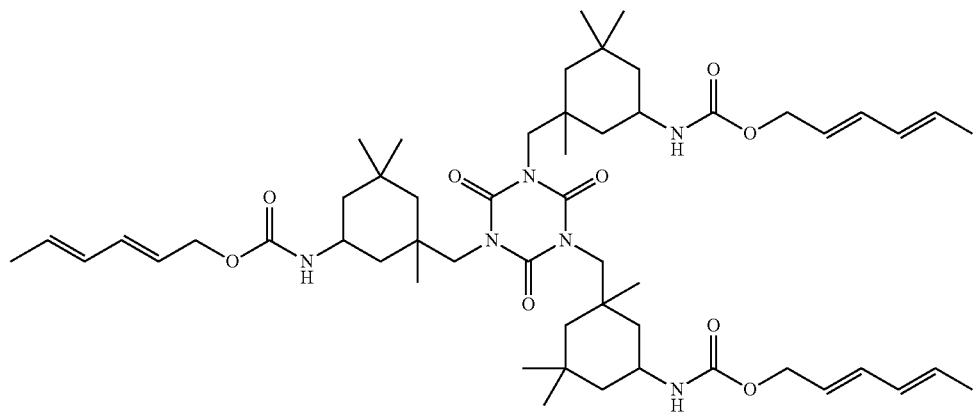

The dienes can be prepared from sorbitol, which is a renewable raw material. These products are sorbic derivatives, which are particularly ecological. The same applies to the retinoids.

The present invention further provides for the use of the compounds of the invention for reversible or permanent crosslinking with compounds having at least one reactive double bond, also referred to below as dienophiles.

Dienophiles are defined as being those compounds which possess a reactive double bond, the double bond being able to react by means of a Diels-Alder reaction with the two double bonds of the reaction products of the invention. This reaction also proceeds in the opposite direction, to form the individual components again: the reaction, accordingly, is reversible and is called a retro-Diels-Alder reaction. In this context, a formulation composed of at least two different components is crosslinked at room temperature by means of a Diels-Alder reaction or a hetero-Diels-Alder reaction. In a second process step, at a higher temperature, at least 50%, preferably at least 90% and more preferably at least 99% of the crosslinking sites are parted again by means of a retro-Diels-Alder reaction or a retro-hetero-Diels-Alder reaction, respectively.

In one preferred embodiment the dienophile component is a difunctional polymer prepared by means of atom transfer radical polymerization (ATRP). In this case the functionalization with the diene groups takes place by a substitution reaction, polymer-analogous or carried out during termination, of terminal halogen atoms. This substitution may take place, for example, by addition of mercaptans functionalized with diene groups.

The dienophile is preferably a compound having a carbon-sulphur double bond and hence the preferred crosslinking reaction is a hetero-Diels-Alder reaction.

In the same preferred embodiment, the dienophile component used may be a low molecular mass organic compound having 3 to 4 dithioester groups, which in accordance with the details above has a group Z which greatly reduces the electron density of the C=S double bond.

With particular preference the dienophile is a dithioester.

With very particular preference the dienophile is a compound having the structure

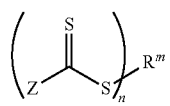

where Z is a—preferably strongly—electron-withdrawing group, $R'''$ is a polyvalent organic group, preferably based on branched or linear alkylic, aromatic or a combination of alkylic and aromatic polyfunctional alcohols, polyfunctional halogenated compounds, polyfunctional carboxylic acids or polyfunctional amines. Alternatively $R'''$ may also be a polymer. The number of dithioester groups n is a number between 2 and 20, preferably between 2 and 10 and more preferably between 2 and 4.

In one preferred embodiment the group Z is a 2-pyridyl group, a phosphoryl group or a sulphonyl group. Additionally contemplated are cyano or trifluoromethyl groups and also any other group Z which very strongly reduces the electron density of the C=S double bond and hence allows a rapid Diels-Alder reaction.

The reversibly or permanently crosslinkable polymers obtainable simply as a result of these crosslinker molecules of the invention are of great interest for a broad field of applications. As examples of re-partable adhesive applications, there have been descriptions, as the skilled person is well aware, of diverse possibilities for the automotive industry or for the semiconductor industry. Adhesives of this kind are also of interest, however, in the construction of machinery, precision mechanical instruments or in the building industry. The formulations and processes of the invention can be used in a very wide variety of application areas. The following list shows a number of preferred application areas by way of example, without restricting the invention in any way in this respect. Examples of such preferred application areas are adhesives, moulding compounds, inks, sealants, coating materials such as varnishes or paints, composite materials, or use in the production of mouldings for example via rapid prototyping methods.

One example of applications in the rapid prototyping sector for the crosslinking and uncrosslinking materials described here is to be found in the sector of FDM (Fused Deposition Modelling) or in 3D printing by inkjet methods using low-viscosity melts.

The examples below describe the invention and also its operability in closer detail.

EXAMPLES

Preparation Descriptions of Sorbic Alcohol-IPDI Adducts and Sorbic Alcohol-T1890 Adducts

Example 1

IPDI-Sorbic Alcohol Adduct (IPDI=Isophorone Diisocyanate) 2

| | |
|---|---|
| 1 mol IPDI | 222.2 g |
| 2 mol sorbic alcohol | 196.3 g |
| 0.01% DBTL | 0.042 g |
| 0.2% Jonol CP | 0.839 g |
| Acetone | 100.0 g |

Sorbic alcohol was melted (60° C.) in a 500 ml three-necked flask and introduced with DBTL (dibutyltin dilaurate), Jonol CP and acetone. The mixture was then heated to 40° C. Subsequently IPDI was added dropwise over the course of 3 hours at 40° C. The reaction mixture was NCO-free after 6 hours at 40° C.=0.67% by weight; after stirring at 40° C. for a further 6 hours, the NCO content was 0.12% by weight. Thereafter the acetone was removed at 40° C. in a vacuum drying cabinet and the solid obtained was ground. m.p.: 80-85° C.

Example 2

VESTANAT T1890 (Trimer of IPDI)-Sorbic Alcohol Adduct

| | |
|---|---|
| 1 mol T1890/100 | 736.8 g |
| 3 mol sorbic alcohol | 294.4 g |
| 0.01% DBTL | 0.103 g |
| 0.2% Jonol CP | 2.06 g |
| 50% Acetone | |

Sorbic alcohol, DBTL and Jonol CP were dissolved in acetone (50% strength). Then IPDI-T1890 was dissolved to 50% strength in acetone and added dropwise to the sorbic alcohol solution over the course of 2 hours at 40° C., followed by stirring at 16 hours—NCO content=0.1% by weight. The acetone was removed at 40° C. in a vacuum drying cabinet. The solid obtained was ground.

Diels-Alder Reaction

Materials

Isophorone bis(sorbylcarbamate) (IPDI-SA) (Evonik Industries AG),
1,4-bis(Bromomethyl)benzene (97%, Aldrich),
Sodium hydride (60% dispersion in mineral oil, Aldrich),
Tetrahydrofuran (THF, anhydrous, ≥99.9%, ABCR),
Diethyl phosphate (>99.0%, Fluka),
Carbon disulphide (anhydrous, ≥99.9%, Aldrich),
Zinc 2-ethylhexanoate (97%, Aldrich) and
Acetonitrile (anhydrous, 99.8%, Fluka) were used in the as-supplied state.

Zinc chloride (Aldrich) was vacuum-dried and stored under an inert gas atmosphere.

All of the other solvents were used without further purification.

Characterizations.

The $^1$H nuclear spin resonance (NMR) spectroscopy was carried out for hydrogen nuclei using a Bruker AM 250 spectrometer which was operated at 500 MHz. All of the samples were dissolved either in CDCl$_3$ or DMSO-d$_6$. The δ scale was calibrated to the internal standard trimethylsilane (TMS, δ=0.00 ppm).

Gel permeation chromatography (GPC) measurements were carried out on a Polymer Laboratories (Varian) PL-GPC 50 Plus Integrated System, which comprised an autosampler, a 5 µm bead size PL-Gel preliminary column (50×7.5 mm), a 5 µm mixed PL-Gel E-column (300×7.5 mm), three 5 µm mixed PL-Gel C columns (300×7.5 mm) and a differential refractive index detector, using THF as eluent at 35° C. and a flow rate of 1 mL min$^{-1}$. The SEC system was calibrated with linear poly(styrene) standards, ranging from 160–6×10$^6$ g mol$^{-1}$, and linear poly(methyl methacrylate) standards, ranging from 700–2×10$^6$ g mol$^{-1}$. Molecular weights relative to PS are reported in the present study.

Mass spectrometry was carried out on an IXQ mass spectrometer (ThermoFisher Scientific) which was equipped with an ionization source under atmospheric pressure that operated in the atomizer-assisted electrospray mode, which was used in positive ion mode. The instrument was calibrated in the m/z range 195-1822 by means of a standard containing caffeine, Met-Arg-Phe-Ala acetate (MRFA) and a mixture of fluorinated phosphazenes (Ultramark 1621) (Aldrich). Samples (c=0.1-0.2 mg mL$^{-1}$) were dissolved in a 3:2 v/v mixture of THF and methanol, doped with sodium acetate (0.014 mg mL$^{-1}$). All of the spectra were obtained within the m/z range of 150-2000 with a spray voltage of 5 kV and a capillary temperature of 275° C. Nitrogen was used as the inert gas (flow rate: not more than 45%) and helium was used as an auxiliary gas (flow rate: not more than 5%). The theoretical mass calculations were carried out using the IsotopeViewer software, version 1.0.

Synthesis of 1,4-phenylenebis(methylene)bis((diethoxyphosphoryl)methanedithio-formate) (P-di-linker) (1)

P-di-linker 1 was synthesized by the following procedure. A solution of diethyl phosphite (5.3 mL, 41.2 mmol) in anhydrous THF (20 mL) was added dropwise under nitrogen to a suspension of NaH (1.64 g, 41.2 mmol) in THF (40 mL) in a two-necked flask which was provided with a reflux condenser and a magnetic stirrer. As soon as the evolution of hydrogen was at an end, the mixture was heated under reflux for 10 minutes. After cooling to room temperature, the mixture was cooled further in a liquid nitrogen bath. CS$_2$ (12.26 mL, 203.6 mmol) was then added dropwise and the mixture was allowed to warm to room temperature. Stirring was continued for 30 minutes more, after which 1,4-bis(bromomethyl-benzene) (5.44 g), dissolved in anhydrous THF (40 mL), was added dropwise to the reaction mixture. Stirring was continued at room temperature for 3 hours and then 200 mL of hexane were added, and the reaction mixture was filtered. The violet filtrate was collected and the solvent was removed under reduced pressure. The crude product was purified by column chromatography on silica gel, initially with hexane as eluent, to remove impurities, and then with ethyl acetate as eluent, to collect the product 1. Following removal of the solvent under reduced pressure, the P-di-linker 1 was obtained as a solid (60% yield) with a dark fuchsia colour. $^1$H NMR (250 MHz, DMSO-d$_6$, 25° C.): δ (ppm)=7.36 (s, 4H, ArH), 4.57 (s, 4H, —CH$_2$S—), 4.21-4.08 (m, 8H, —OCH$_2$CH$_3$), 1.30-1.21 (t, J=7 Hz, 12H, —CH$_2$CH$_3$). ESI-MS+Na (m/z) calculated 553.01; found 553.12.

Scheme 1. Synthesis of phosphoatedithioester di-linker 1.

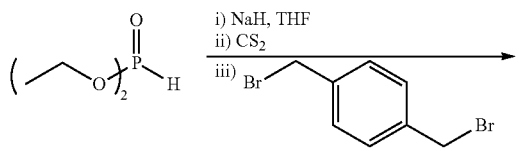

was 1.8 M. The reaction mixture was admixed with 1.1 equivalents of zinc chloride (ZnCl$_2$). This mixture was heated at 50° C. for 4 hours. The viscous mixture was diluted in 1 mL of chloroform, extracted with water to remove ZnCl$_2$, and dried (85-96% yield). This staged polymerization reaction was carried out in the presence of acetonitrile, to give the product 3. The product was analysed by SEC. $M_n$=8100 g mol$^{-1}$ after 2 hours.

Scheme 2. The cycloaddition product 3 (simplified structure of one possible regio/stereoisomer shown), which is formed from the HDA reaction of 1 and 2.

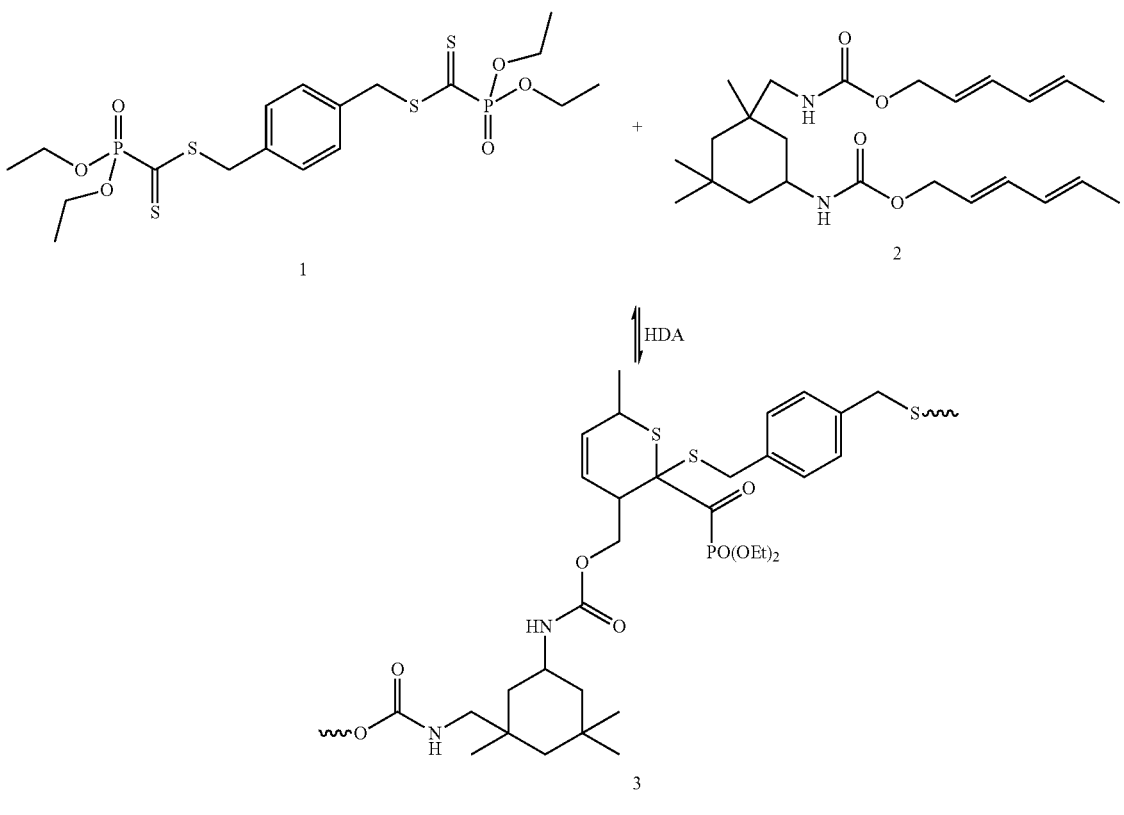

-continued

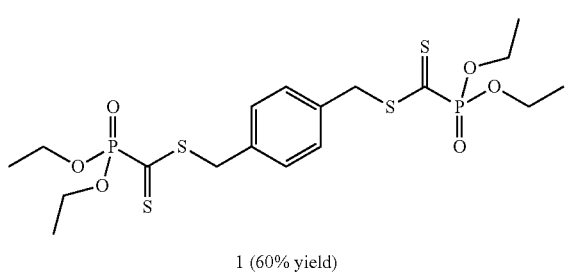

1 (60% yield)

Diels-Alder Reaction: Staged Polymerization of P-Di-Linker 1 and IPDI-SA 2, Leading to Product 3.

A typical polymerization procedure was as follows: both IPDI-SA and P-di-linker were dissolved separately in acetonitrile and mixed in a ratio of 1:1, based on functional groups, such that the concentration of the resulting solution Retro-Diels-Alder Reaction (rDA) of 3.

A typical reaction procedure was as follows: 100 mg of polymer 3 were dissolved in 5 mL of acetonitrile. With stirring, the solution was heated at 140° C. in a pressure tube for 40 minutes. The temperature was varied from 120-160° C. and the reaction time was varied from 10 minutes to 160 minutes. The reaction mixture was then quenched rapidly with liquid nitrogen. A sample (0.1 mL) of the rDA product was diluted in THF (0.4 mL) and analysed by GPC and mass spectrometry. The results are shown in FIG. 1.

The invention claimed is:
1. A reaction product obtained by a process comprising: reacting
   A) comprises at least one diamine selected from the group consisting of 1,3-diaminomethylcyclohexane, 1,4-diaminomethylcyclohexane, hexane-1,6-diamine, 2,2,4-trimethylhexane-1,6-diamine, 2,4,4-trimethylhexane-1,6-diamine, 3-aminomethyl-3,5,5-trimethylcyclohexylamine, 4,4'-methylenedicyclohexyldiamine, 2,4- methylenedicyclohexyldiamine, 2,2'-methylenedicyclohexyldiamine, and a polyetherdiamine with B) at least one diene comprising a functional group of formula (II)

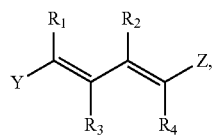
(II)

wherein:

Y is CH$_2$OH, COOH or COOA,

Z and each of R$^1$-R$^4$ are independently, an alkyl radical comprising from 1 to 16 carbon atoms, a cyclic hydrocarbon radical or an aromatic hydrocarbon radical, and the alkyl radical, the cyclic hydrocarbon radical, or the aromatic hydrocarbon radical optionally comprises at least one of a heteroatom, a functional group, and a double bond, optionally each of R$^1$-R$^4$ being independently hydrogen;

where each A in Y is, independently, an alkyl radical comprising from 1 to 16 carbon atoms, a cyclic hydrocarbon radical or an aromatic hydrocarbon radical, and the alkyl radical, the cyclic hydrocarbon radical, or the aromatic hydrocarbon radical optionally comprises at least one of a heteroatom and a double bond, and wherein a covalent bond forms between A) and B) upon said reacting.

2. The reaction product according to claim 1, wherein the reaction product is obtained by a process comprising: reacting component A), component B) and at least one isocyanurate.

3. The reaction product according to claim 1, wherein component B) is at least one of sorbic alcohol and sorbic acid.

4. The reaction product according to claim 1, wherein component B) is a retinoid of formula (V):

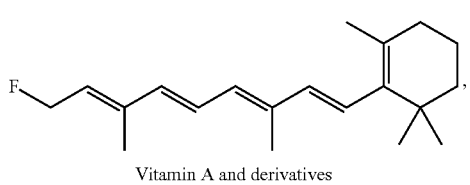
(V)

Vitamin A and derivatives

F is OH, COOH, or COOK, and

K is an alkyl radical comprising from 1 to 6 carbon atoms, a cyclic hydrocarbon radical or an aromatic hydrocarbon radical, and optionally comprises at least one of a heteroatom, a functional group, and a double bond.

5. The reaction product according to claim 4, wherein component B) is a retinoid of formula (VI):

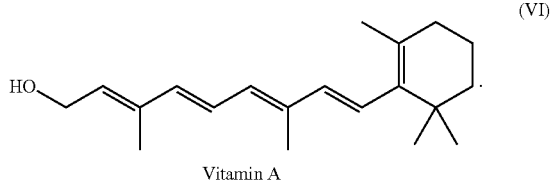 [SMILES: CC1=C(/C=C/C(C)=C/C=C/C(C)=C/CO)C(C)(C)CCC1]
(VI)

Vitamin A

6. The reaction product according to claim 1, where each A in Y is, independently, an alkyl radical comprising from 1 to 16 carbon atoms, a cyclic hydrocarbon radical or an aromatic hydrocarbon radical, and the alkyl radical, the cyclic hydrocarbon radical, or the aromatic hydrocarbon radical optionally comprises a double bond.

7. A method for producing an article, the method comprising:

reversibly or permanently crosslinking the reaction product according to claim 1 with a dienophile component compound comprising a reactive double bond, thereby obtaining the article.

8. The method according to claim 7, wherein the dienophile component compound is a difunctional polymer prepared by atom transfer radical polymerization.

9. The method according to claim 7, wherein the dienophile component compound is a compound comprising a carbon-sulphur double bond.

10. The method according to claim 7, wherein the dienophile component compound is a dithioester.

11. The method according to claim 7, wherein the dienophile component compound comprises

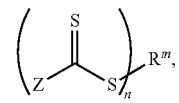

Z is an electron-withdrawing group,

R$^m$ is a polyvalent organic group, and n is a number from 2 to 20.

12. The method according to claim 11, wherein R$^m$ is a polyvalent organic group based on branched or linear alkylic, aromatic or a combination of alkylic and aromatic polyfunctional alcohols, polyfunctional halogenated compounds, polyfunctional carboxylic acids, polyfunctional amines, or a polymer.

13. The method according to claim 11, wherein Z is a 2-pyridyl group, a phosphoryl group, a sulphonyl group, a cyano group or a trifluoromethyl group.

14. The method according to claim 7, wherein the article is an adhesive, a moulding compound, an ink, a sealant, a coating material, a varnish, a paint, or a composite material.

15. The method according to claim 7, wherein the article is a moulding, and said crosslinking is optionally carried out via rapid prototyping methods.

16. The method according to claim 7, wherein component B) is at least one of sorbic alcohol and sorbic acid.

17. The method according to claim 7, wherein component B) is a retinoid of formula (V):

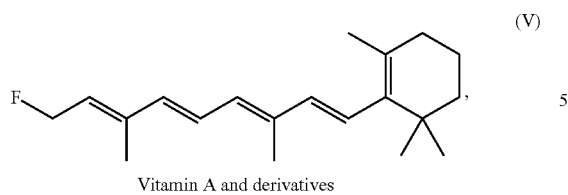
Vitamin A and derivatives
F is OH, COOH or COOK, and
K is an alkyl radical comprising from 1 to 6 carbon atoms, a cyclic hydrocarbon radical or an aromatic hydrocarbon radical, and optionally comprises at least one of a heteroatom, a functional group, and a double bond.
18. The method according to claim 17, wherein component B) is a retinoid of formula (VI):
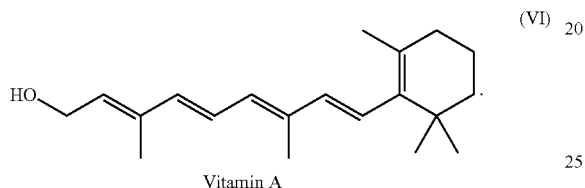
Vitamin A
* * * * *